United States Patent [19]

Fritsch et al.

[11] 4,191,765
[45] Mar. 4, 1980

[54] 1-ARYLOXY-2-HYDROXY-3-AMINOPRO-PANES

[75] Inventors: Werner Fritsch, Bad Soden am Taunus; Ulrich Stache, Hofheim am Taunus; Ernst Lindner, Frankfurt am Main, all of Fed. Rep. of Germany

[73] Assignee: Hoechst Aktiengesellschaft, Frankfurt am Main, Fed. Rep. of Germany

[21] Appl. No.: 932,504

[22] Filed: Aug. 10, 1978

Related U.S. Application Data

[63] Continuation-in-part of Ser. No. 799,676, May 23, 1977, abandoned.

[30] Foreign Application Priority Data

May 25, 1977 [DE] Fed. Rep. of Germany ..... 26233147

[51] Int. Cl.$^2$ ............... A61K 31/215; A61K 31/275; C07C 69/76; C07C 121/80
[52] U.S. Cl. ..................... 424/248.53; 260/326.47; 260/326.5 M; 260/340.5 R; 260/465 E; 260/501.17; 544/163; 544/171; 544/230; 544/238; 544/360; 544/383; 544/394; 544/399; 544/401; 546/194; 546/230; 546/238; 560/21; 560/42; 562/435; 562/451; 424/248.55; 424/248.58; 424/250; 424/267; 424/274; 424/282; 424/304; 424/309; 424/316; 424/317
[58] Field of Search ............ 260/465 E; 560/42; 544/163, 171, 230, 238, 360, 394, 399; 424/304, 309, 248.53, 248.55

[56] References Cited

U.S. PATENT DOCUMENTS

| | | | |
|---|---|---|---|
| 3,644,469 | 2/1972 | Koppe et al. | 260/465 E |
| 3,663,607 | 5/1972 | Barrett et al. | 560/42 |
| 3,857,873 | 12/1974 | Schwender et al. | 560/42 |
| 4,014,920 | 3/1977 | Jaeggi et al. | 260/465 E |

*Primary Examiner*—Dolph H. Torrence
*Attorney, Agent, or Firm*—Curtis, Morris & Safford

[57] ABSTRACT

Compounds of formula I

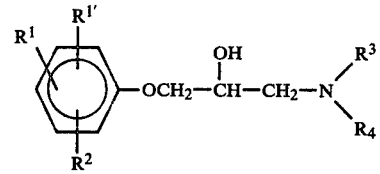

wherein $R^1$ and $R^{1'}$ are identical or different and represent hydrogen, an alkyl radical or alkoxy radical having 1–4 carbon atoms, the allyl group, a halogen atom or the nitro group, $R^2$ represents an acrylic acid radical or an acrylic acid nitrile radical of the formulae

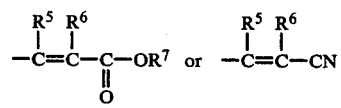

wherein $R^5$ represents hydrogen, an alkyl radical having 1–5 carbon atoms, an aryl radical or aryl-lower alkyl radical either unsubstituted or substituted by lower alkyl or alkoxy, $R^6$ represents hydrogen or an alkyl radical having 1–8 carbon atoms, $R^7$ represents hydrogen, a lower alkyl radical or an aryl-lower alkyl radical, $R^3$ and $R^4$ represent together with the nitrogen atom a heterocyclic ring with 5–7 members being optionally substituted by $C_1$–$C_4$ alkyl, in which ring one carbon atom may be replaced by one oxygen atom, sulfur atom or one further nitrogen atom, the latter may be substituted, or wherein $R^3$ represents hydrogen and $R^4$ represents a phenyl-alkylene or phenyl-alkylidene radical of the formula

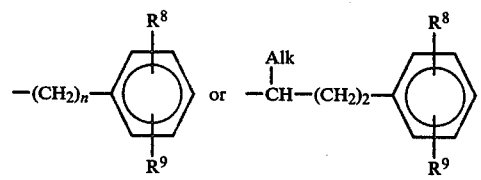

in which Alk is alkyl having 1 to 3 carbon atoms, and n is a figure from 1–3, and $R^8$ and $R^9$ are identical or different and represent hydrogen, an alkoxy radical having 1–3 carbon atoms or the benzoyl radical or $R^8$ and $R^9$ represent together the bismethylene dioxy radical, as well as the physiologically compatible acid addition salts and a process for preparing these compounds.

6 Claims, No Drawings

1-ARYLOXY-2-HYDROXY-3-AMINOPROPANES

This is a continuation-in-part of application Ser. No. 799,676 filed May 23, 1977 now abandoned.

The present invention relates to basically substituted phenol ethers of the formula I

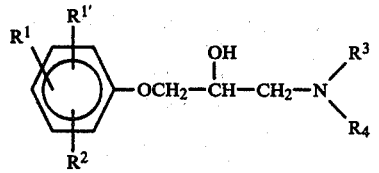

in which $R^1$ and $R^{1'}$ are identical or different and represent hydrogen, an alkyl or alkoxy radical containing 1–4 carbon atoms, the allyl group, a halogen atom or the nitro group, $R^2$ represents an acrylic acid radical or acrylic acid nitrile radical having respectively the formulae

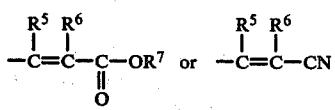

in which $R^5$ represents hydrogen, a $C_1$–$C_5$-alkyl radical, an aryl or aryl-lower alkyl radical which is unsubstituted or substituted by lower alkyl or alkoxy, $R^6$ represents hydrogen or an alkyl radical containing 1–8 carbon atoms, and $R^7$ represents hydrogen, a lower alkyl radical or an aryl-lower alkyl radical, $R^3$ and $R^4$ together with the nitrogen atom represent a heterocyclic ring containing 5–7 members optionally substituted by $C_1$–$C_4$-alkyl, in which ring a carbon atom may be replaced by an oxygen atom, sulphur atom or a further nitrogen atom, and the latter may be substituted by an alkyl, alkoxy, oxalkyl, acyl or carbalkoxy residue in each case containing 1 to 5 carbon atoms, a pyridyl radical or a phenyl radical, which may itself be substituted one or more times by the hydroxyl group, halogen or an alkyl or alkoxy radical containing 1 to 4 carbon atoms, or $R^3$ represents hydrogen and $R^4$ represents a phenyl-alkylene or phenyl-alkylidene radical of the formula

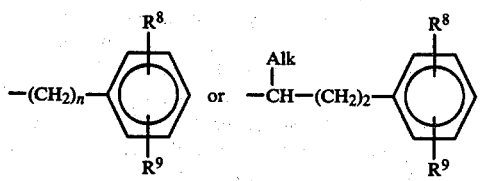

in which Alk is alkyl having 1 to 3 carbon atoms, n is a number from 1 to 3, and $R^8$ and $R^9$ are identical or different and represent hydrogen, an alkoxy radical containing 1 to 3 carbon atoms or the benzyloxy radical, or $R^8$ and $R^9$ together represent a bismethylene-dioxy radical, and also physiologically tolerable acid addition salts thereof.

The invention includes both the racemic mixtures and the individual optically active isomers of the formula I.

The present invention is also concerned with a process for the production of compounds of the formula I, which is characterised in that (a) a compound of the formula II

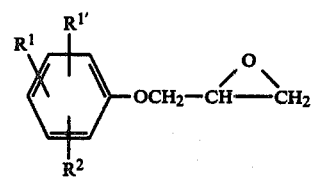

in which $R^1$, $R^{1'}$ and $R^2$ have the meanings given for formula I, is reacted with an amine of the formula III

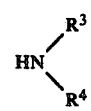

in which $R^3$ and $R^4$ have the meanings given for formula I, or (b) a compound of the formula IV

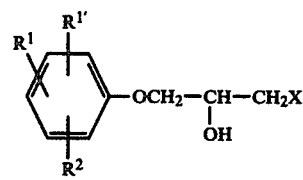

in which $R^1$, $R^{1'}$ and $R^2$ have the meanings given for formula I, and X represents a halogen atom, the sulphuric acid radical or a sulphonic acid radical, is reacted with an amine of the general formula III, or (c) a compound of the formula V

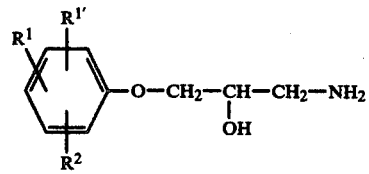

in which $R^1$, $R^{1'}$ and $R^2$ have the meanings given for formula I, is reacted with a compound of the formula VI $$X-R^4 \qquad \text{VI}$$

in which $R^4$ has the meaning given for formula I and X has the meaning given for formula IV, or (d) a phenol of the formula VII

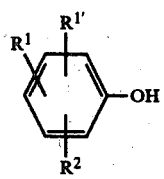

in which $R^1$, $R^{1'}$ and $R^2$ have the meanings given for formula I, is reacted with a compound of the formula VIII

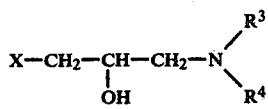

in which $R^3$ and $R^4$ have the meanings given for formula I and X has the meaning given for formula IV, in the presence of an acid-binding agent, or (e) a compound of the formula V or IX

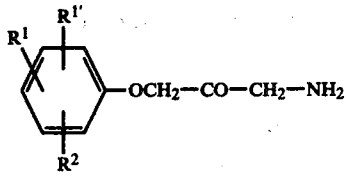

in which $R^1$, $R^{1'}$ and $R^2$ have the meanings given for formula I, is reacted with a suitable ketone and the condensation product is reduced, or (f) a compound of the formula X

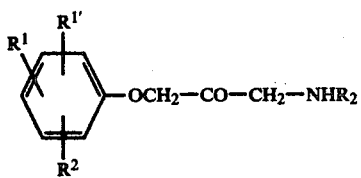

in which $R^1$, $R^{1'}$, $R^2$ and $R^4$ have the meanings given for formula I, is reduced, or (g) a compound of the formula XI

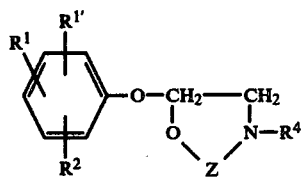

in which $R^1$, $R^{1'}$, $R^2$ and $R^4$ have the meanings given for formula I and Z represents a carbonyl group or a methylene group optionally substituted by a phenyl group or one or two lower alkyl radicals, is hydrolysed, or (h) in a compound of the formula XII

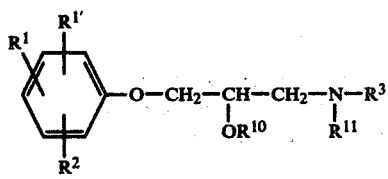

in which $R^1$, $R^{1'}$, $R^2$ and $R^3$ have the meanings given for formula I, $R^{10}$ represents hydrogen, a lower acyl radical or the benzyl radical, and $R^{11}$ represents hydrogen or the benzyl radical, but $R^{10}$ and $R^{11}$ cannot both simultaneously represent hydrogen, the benzyl groups are split off by catalytic hydrogenation in the presence of a noble metal and/or the acyl group is hydrolysed, and the compounds obtained in accordance with methods (a) to (h) are optionally converted into physiologically tolerable acid addition salts.

Among the substituents mentioned the following are preferred:

For $R^4$ (when $R^3$=H): dialkoxyphenyl-ethylidene radicals, especially the 5',4'-dimethoxyphenyl-ethylidene radical or the 1-methyl-2-3',4'-dimethoxyphenyl-ethylidene radical.

When $R^3$ and $R^4$ together with the nitrogen atom form a heterocyclic ring, there are preferred as ring systems those containing 5 or 6 members, for example, pyrrolidine, piperidine and morpholine, which may be substituted once or twice by a lower alkyl radical or substituted by the pyridyl radical. Especially preferred is the piperazine ring, which may be substituted at the second nitrogen atom by an alkyl, alkoxy, oxalkyl or acyl group containing 1-4 carbon atoms, by a carbalkoxy group containing 1-5 carbon atoms, by a pyridyl radical or by an optionally substituted phenyl radical.

For $R^5$: hydrogen, an unbranched alkyl radical containing 1-4 carbon atoms, especially the methyl, ethyl radical, and the phenyl radical, For $R^6$: hydrogen, an alkyl radical containing 1-4 carbon atoms, For $R^7$: an alkyl radical containing 1 to 4 carbon atoms, especially the methyl, ethyl and tert.-butyl radical, and also the benzyl radical.

For $R^1$ and $R^{1'}$: hydrogen, alkyl or alkoxy radicals containing 1-3 carbon atoms, fluorine, chlorine and also the nitro group.

As amines of the formula III there come into consideration for the reactions according to methods (a) and (b): 1. Primary amines, such, for example, as phenylethylamine, 3-phenyl-propylamine, 1-phenyl-ethylamine, 1-methyl-2-phenyl-ethylamine, 1-methyl-2-(4-methoxy)-phenylethylamine, 1-methyl-2-(3,4-dimethoxy)-phenylethylamine, 3,4-dimethoxyphenylethylamine, 3-methoxy-4-ethoxy-phenylethylamine, 3-methoxy-4-hydroxy-phenylethylamine, 3-methoxy-4-benzyloxy-phenylethylamine, 3-benzyloxy-4-methoxy-phenylethylamine, 3,4-methylenedioxy-phenylethylamine, 2,5-dimethoxyphenylethylamine, 2,4-dimethoxyphenylethylamine, 2,3-dimethoxyphenylethylamine, 3,4,5-trimethoxy-phenylethylamine, 2-methoxyphenylethylamine, 3-methoxyphenylethylamine, 4-methoxyphenylethylamine, 3,4-dimethoxyphenylmethylamine, 2-hydroxy-2-phenyl-ethylamine, 1-methyl-2-hydroxy-2-phenylethylamine, 3,4-dimethylphenylethylamine, 4-chlorophenylethylamine, 3,4-dichlorophenylethylamine, 4-hydroxyphenylethylamine and correspondingly substituted phenyl-propylamines. Homoveratrylamine and 1-methyl-3-phenyl-propylamine have been found especially advantageous. 2. 5-6 Membered cyclic secondary amines such, for example, as: Phenylpiperazine, N-2'-methylphenylpiperazine, N-3'-methylphenylpiperazine, N-4'-methylphenylpiperazine, N-2'-methoxyphenylpiperazine, N-3'-methoxyphenylpiperazine, N-4'-methoxyphenylpiperazine, N-2'-chlorophenylpiperazine, N-3'-chlorophenylpiperazine, N-4'-chlorophenylpiperazine, N-2'-pyridylpiperazine, N-3'-pyridylpiperazine, N-4'-pyridylpiperazine, N-2'-hydroxyphenylpiperazine, N-3'-hydroxyphenylpiperazine, N-4'-hydroxyphenylpiperazine, N-oxyethylpiperazine, N-methylpiperazine, N-ethylpiperazine, N-carbomethoxypiperazine, N-carbethoxypiperazine, N-carbo-(2-hydroxy-2-methyl)-propoxypiperazine, 2-methylpiperazine, 2,6- dimethylpiperazine, 2,6-dimethylpiperidine, 3-β-pyridylpiperidine, piperidine, morpholine and also pyrrolidine.

The introduction of the amine radical according to method (a) is carried out by reaction of the two components, optionally in the presence of organic solvents such as alcohols, for example, methanol, ethanol, isopropanol, aromatic solvents such as benzene, toluene or ethers such as dioxane, tetrahydrofurane or carboxylic acid amides, especially dimethylformamide. In a preferred modification the two components dissolved in alcohol may be reacted with one another at a raised temperature. As reaction temperatures there come into consideration temperatures from room temperature up to the boiling point of the solvent.

The glycidyl ethers of the formula II used as starting materials in method (a) can be obtained in the following way:

A compound of the formula XIII

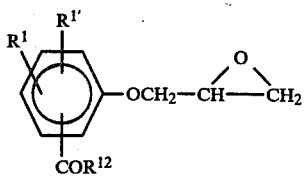

wherein $R^1$ and $R^{1'}$ have the meanings given for formula I and $R^{12}$ represents hydrogen, a $C_1$-$C_5$-alkyl radical or the benzyl radical, is reacted according to Wittig-Horner with a phosphonate carbanion of the formula

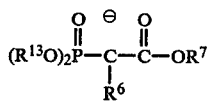

wherein $R^6$ and $R^7$ have the meanings given for formula I and $R^{13}$ represents a lower alkyl group or a phenyl group.

In order to effect this synthesis of 1-aryloxy-2,3-epoxy-propanes of formula II, the compounds of formula XIII are reacted preferably with carbalkoxymethyldialkyl- or cyanomethyldialkyl phosphonates in the presence of anhydrous bases in inert organic solvents. Preferably, carbmethoxymethyl-, carbethoxymethyl-, carbbenzoxymethyl-, dimethyl- or diethyl-phosphonates, [β-methyl-carbethoxy-methyl]-diethyl phosphonate, cyanomethyldimethyl- or diethyl phosphonate, [β-methyl-cyanomethyl]-diethyl phosphonate are used as phosphonates.

The phosphonates used may be produced, e.g., according to the method described in G. M. Kosolapoff- "Organophosphorus Compounds" (Wiley and Sons, Inc., New York, N.Y. (1950), chap. 7) by reactions of the alkyl radicals, correspondingly halogenated in the β-position, with triethyl phosphite. There are mainly used as bases alkali metal and alkaline earth metal hydrides and amides as well as alkali metal and alkaline earth metal alcoholates, preferably sodium or potassium hydride but also sodium or potassium amide and sodium or potassium tert.-butylate.

Suitable inert solvents are alcohols, hydrocarbons, but preferably aprotic solvents, such as, for example, ethers (tetrahydrofuran, dioxan, dimethoxy glycol, diglym), dimethylformamide, dimethyl sulfoxide or mixtures of the solvents mentioned.

In order to effect the process, 1 mol equivalent of a compound of formula II is dissolved or suspended in one of the solvents indicated, preferably in an aprotic solvent. 1-10, preferably 1-4, mole equivalents of the alkali metal or alkaline earth metal compound of one of the phosphonates indicated are then added to one of the solvents indicated, preferably in an aprotic solvent, at 0°-30° C., while cooling if necessary. The alkali metal or alkaline earth metal phosphonates are prepared according to known methods. In a particularly advantageous embodiment, a stoichiometric quantity of sodium hydride in one of the aprotic solvents indicated, for example, in tetrahydrofuran or dioxan, and one of the phosphonates mentioned is added dropwise until the sodium hydride dissolves or until the evolution of $H_2$ is complete.

The reaction solution is then stirred at a temperature between −40° C. and the boiling point of the solvent used, preferably at temperatures between 0° C. and 50° C. The reaction times may be between 1 minute and approximately 72 hours but the reaction is generally complete after between 30 minutes and 7 hours.

The procedure may also be reversed, the solution or suspension of the compound of formula II being added to the solution of the alkali metal or alkaline earth metal phosphonate. However, the procedure may also be such that the base, preferably an alkali metal hydride or amide, is suspended in the solution or suspension of the compound of formula II in one of the aprotic solvents indicated, preferably in an ether, and the phosphonate is then added and the reaction mixture further treated as usual. The dissolution, occurring later in this case, of the alkali metal hydride or amide and the $H_2$ evolution connected therewith, do not impair the olefination reaction.

The products of the process are isolated according to normal methods of operation. After the reaction has terminated, the reaction mixtures are added to salt-containing water and, where there is sufficient lipoid solubility of the products, these are precipitated in solid or oily form. Water-soluble products thereby largely dissolve. In so far as the products cannot be separated by filtering off, they are isolated in the normal manner by extraction with a water-insoluble solvent, for example, chloroform or methylene chloride, to which a small quantity of a lower alcohol is advantageously added. After the solvents have been removed, the products are in solid or oily form. They can generally be obtained in a pure state in crystallized or amorphous form by recrystallizing or dissolving and reprecipitating from suitable organic solvents. The products can also be obtained in a pure form by normal chromatography.

The starting compounds of formula XIII can be produced according to normal methods by reacting a correspondingly substituted hydroxybenzene derivative, having a keto function in the o-, m- or p-position, with epichlorohydrin.

In the method described under (b) the α-halogen-β-hydroxy-propyl ethers of the formula IV are used as starting materials. Instead of the halogen atom, preferably chlorine or bromine, in the α-position there may be used the corresponding esters of sulphuric acid or esters of sulphonic acids.

The starting substances can also be obtained by splitting the epoxide of the formula II with a hydrohalic acid, sulphuric acid or sulphonic acid. The reaction with an amine of the formula III is carried out in the presence or absence of suitable organic solvents, such as alcohols, for example, methanol, ethanol, isopropanol, aromatic solvents such as benzene, toluene, or ethers such as dioxane, tetrahydrofurane, or carboxylic acid amides, especially dimethylformamide. The reaction may be carried out at temperatures between room temperature and the boiling point of the solvent, and is preferably carried out at a raised temperature. For binding the liberated acid, for example halogen hydride, the operation may be carried out in the presence of acid-binding agents, for example, tert.-amines, such as triethylamine, pyridine or alkali or alkaline earth metal hydroxides, carbonates or bicarbonates. The amine used can advantageously be used for the reaction in excess, for example, in twice the molar quantity.

For the method described under (c) there is used the phenoxy-2-hydroxy-1-aminopropane derivative of the formula V.

The latter may also be present in the form of a salt. The reaction with a reactive ester of the formula VI is carried out under the reaction conditions mentioned in method (b). The amine of the formula V used as starting material can be obtained, for example, by reacting the epoxide of the formula II with ammonia. It can also be obtained from the halogen compound IV with ammonia.

The preparation of the products of the process is also effected in accordance with the method described under (d), in which the above-mentioned phenol of the formula VII is used. The phenol may also be used in the form of its alkali metal salts, such as the sodium or potassium salt. As reaction components of the formula VIII there are used 1-halogeno-2-hydroxy-3-alkylaminopropanes. It is also possible to start from sulphuric or sulphonic acid esters of the 1,2-dihydroxy-3-alkylaminopropanes. The reaction is advantageously carried out in the presence of an acid-binding agent, such as an alkali metal hydroxyde. In an alkaline medium the 1-halogeno-2-hydroxy-3-alkylaminopropane used can change intermediately into the corresponding 1,2-epoxypropane, which reacts with the phenol. The reaction may be carried out in the presence or absence of solvents such, for example, as alcohols, for example, methanol, ethanol, isopropanol, aromatic solvents such as benzene or toluene, or ethers such as dioxane, tetrahydrofurane, or carboxylic acid amides, especially dimethylformamide, at normal temperature or a raised temperature up to the boiling point of the solvent used. The compounds of the formula VIII used as starting materials are obtainable, for example, by the reaction of an amine of the formula III with epichlorhydrin at low temperatures.

In the method described under (e) the amine of the formula V is hydrogenated with a ketone appropriate for the meaning of $R_4$ in the presence of catalytically activated hydrogen. As ketones there may be mentioned, for example, acetone, methyl ethyl ketone, cyclopropanone and cyclohexanone. As catalysts there are used, for example, Raney nickel, platinum or palladium. Generally, the operation is carried out in the presence of an inert solvent such as methanol, ethanol or isopropanol. It is also possible first to condense the amine of the formula III with the above mentioned ketone and then to reduce as above the Schiff's base so obtained, optionally without isolating it. The reduction of the azomethine may also be carried out in the usual manner with sodium boranate, lithium alanate or other complex metal hydrides, and also with aluminium amalgam.

By the method (e) there are obtained only those compounds of the formula I in which the radical $R_4$ is connected to the nitrogen atom by a secondary carbon atom.

The method described under (e) can also be carried out by using the aminoketone of the formula IX. The reaction is carried out in the same manner as in the case of the aminopropanol of the formula V, since in the reduction, either in one reaction stage or after preparing and optionally isolating the azomethine, the keto group is simultaneously reduced with the azomethine double bond. The preparation of the aminoketone used as starting material may be carried out, for example, by mild oxidation of the aminopropanol of the formula V.

The method described under (f), namely the reduction of aminoketones of the formula X can also be carried out by catalytic hydrogenation in the manner already described for method (e). The reduction of the keto group can also be carried out with lithium alanate or other complex metal hydrides or by the Meerwein-Ponndorf method with aluminium isopropylate. The preparation of the ketones of the formula X can be carried out, for example, by reacting appropriate 1-halogen-2-oxo-3-(phenoxy)-propanes with an amine of the formula III.

A further modification of the process of the invention is the hydrolysis of an oxazolidone or oxazolidine of the formula XI by method (g). Such oxazolidones can be obtained, for example, by reacting the corresponding 1-amino-2-hydroxy-3-(phenoxy)-propanes with a reactive derivative of carbonic acid, such as diethylcarbonate, chlorocarbonic acid methyl ester or phosgene, or by reacting a 5-hydroxymethyl-oxazolidone-(2) optionally appropriately substituted in the 3-position and in the form of a hydrohalic acid ester, a sulphuric acid ester, or a sulphonic acid ester with an appropriate alkyl phenolate. Suitable oxazolidines can be prepared, for example, by reacting the corresponding 1-amino-2-hydroxy-3-phenoxy-propanes of the formula V with aldehydes or ketones. Oxazolidones or oxazolidines not substituted at the nitrogen atom may be alkylated with compounds of the formula VI as described under method (c). The hydrolysis of these oxazolidone derivatives or oxazolidine derivatives may be carried out in an acid or alkaline medium, for example, by means of dilute hydrochloric acid, dilute sulphuric acid, dilute sodium hydroxide solution or dilute potassium hydroxide solution. It is of advantage to apply heat in order to accelerate the hydrolysis. The hydrolysis may also be carried out in water-soluble solvents, for example, lower alcohols. The products of the process can also be obtained from compounds of the formula XII, in which the hydroxyl and/or the secondary amino group is protected by the radical $R^{10}$ or $R^{11}$ respectively, by splitting off these protecting groups. As protecting groups there come into consideration acyl radicals or the benzyl radical. The splitting off of the benzyl radical is carried out by catalytic hydrogenation in the presence of noble metals, such as palladium or platinum. If acyl-compounds are used, the acyl radical preferably being a lower aliphatic acyl radical, such as the acetyl or propionyl radical, the splitting is carried out hydrolytically either in an acid or alkaline aqueous medium. The preparation of the corresponding benzyl- or acyl-compounds of the formula XII may be carried out by one of the methods described above, the corresponding acylated or benzylated starting materials being used. When starting materials of the formula XII are to be prepared, in which $R_2$ represents an acyl radical, a compound of formula III, for example, may be acylated and then the corresponding acyl compounds are reacted by method (b) to form compounds of the formula XII. This applies correspondingly for compounds in which $R^{10}$ represents a benzyl radical, the corresponding hydroxy-compounds being benzylated, instead of acylated. If it is desired to start from compounds of the formula XII, in which $R^{11}$ represents a benzyl radical, there can be used in accordance with methods (a), (b), (c), (f) or (d), instead of the primary amines, the corresponding N-benzyl-compounds. When an acyl radical and a benzyl radical are in juxtaposition as $R^{10}$ and $R^{11}$, these groups can be split off in succession in the manner described.

It may sometimes be of advantage in methods (a), (b), (d) or (h) to combine the preparation of the starting compounds directly with the further reaction, that is to say, not to isolate the starting materials separately.

The products of the process may be obtained in the form of the base or in the form of salts thereof, and when necessary they are purified by the usual methods, for example, by recrystallisation or optionally conversion into the free base and subsequent treatment with a suitable acid. The products of the process may, if desired, be converted into salts of physiologically tolerated organic or inorganic acids.

As organic acids there may be mentioned, for example, acetic acid, malonic acid, propionic acid, lactic acid, succinic acid, tartaric acid, maleic acid, fumaric acid, citric acid, malic acid, benzoic acid, salicylic acid, oxyethane sulphonic acid, aceturic acid, ethylene diamine tetracetic acid, embonic acid and also synthetic resins containing acid groups.

As inorganic acids there come into consideration, for example, hydrohalic acids such as hydrochloric acid or hydrobromic acid, sulphuric acid, phosphoric acid and amido-sulphonic acid.

The optically active isomers of the racemic basically substituted phenol ethers of the formula I can be obtained by splitting the latter into their components with optically active acids.

As acids there come into consideration for the preparation of optically active salts in accordance with the invention, for example, (+)- and (−)-tartaric acid, (+)-and (−)-dibenzoyl-tartaric acid, (+)- and (−)-ditoluyl-tartaric acid, (+)- and (−)-mandelic acid, (+)- and (−)-camphoric acid, (+)-camphor-β-sulphonic acid, (+)-α-bromocamphor-α-sulphonic acid and N-(para-nitrobenzoyl)-(+)-glutamic acid. The preparation of the optically active salts may be carried out in water or aqueous or anhydrous organic solvents. The use of alcohols or esters of organic carboxylic acids has been found advantageous.

For the preparation of optically active compounds, the racemate of the base is reacted in a solvent, preferably in molar proportions, with an optically active acid, and the optically active salt of the compound of the formula I is isolated. In certain cases it is also possible to use only one half of an equivalent of the optically active acid in order to remove one of the optically active antipodes from the racemate, and also quantities of optically active acid in excess may be used.

Depending on the nature of the optically active acid, the desired antipodes can be obtained either directly or from the mother liquor of the first crystallizate. Subsequently, the optically active base may be liberated from the salt in the usual manner, and this optically active base can be converted into a salt of one of the physiologically tolerable organic or inorganic acids mentioned above.

The compounds of the formula I and physiologically tolerable acid addition salts thereof have been found in animal tests on dogs to have valuable therapeutic, especially β-adrenolytic, $β_1$-adrenolytic, and/or blood pressure-lowering and/or anti-arrhythmic properties, and can therefore be used, for example, for the treatment or prophylaxis of disorders of the coronary vessels, for the treatment of cardiac arrhythmia and for the treatment of high blood pressure in human medicine.

Special emphasis may be given to the following:

A therapeutically favourable split between $β_1$- and $β_2$-receptor blocking action, the $β_2$-receptors not being blocked, is exhibited by compounds of the formula I in which $R^4$, when $R^3=H$, represents a phenyl-alkylene radical. For example, the product according to Example 15 exhibits a substantially stronger $β_1$-sympathicolytic (in the absence of $β_2$-sympathicolytic) action than do the known 1-[(3,4-dimethoxyphenethyl)-amino]-3-aryloxy-2-propanols such, for example, as 1-[(3,4-dimethoxyphenethyl)-amino]-3-(meta-tolyloxy)-2-propanol hydrochloride [M. L. Hoefle et. al., J. Med. Chem. 18, 148(1975)].

The products of the process may be administered in the form of free bases or salts thereof orally in the form of tablets or dragees, optionally mixed with the usual pharmaceutical carrier substances and/or stabilizers or parenterally in the form of solutions in ampoules. As carrier substances for tablets there come into consideration, for example, lactose, starch, tragacanth and/or magnesium stearate.

For injection purposes there comes into consideration a dosage of about 2–20 mg, and for peroral dosage between about 6 and 150 mg. A single tablet or a dragee may contain about 5 to 50 mg of active substance.

A therapeutic similarly desired long-lasting significant lowering of the blood pressure with only little or no β-receptor blocking is exhibited by compounds of the formula I, in which $R^3$ together with $R^4$ and the N-atom represent a heterocycle such as piperidino, morpholino, unsubstituted piperazino, or piperazino substituted at the second N-atom.

The following Examples illustrate the invention.

EXAMPLE 1

[D,L]-3-[2-(3-Morpholino-2-hydroxy-propoxy)-phenyl]-crotonic acid nitrile hydrochloride 15 Grams of [D,L]-3-[2-(2,3-oxido-propoxy)-phenyl]-crotonic acid nitrile in a mixture of 90 ml of ethanol and 6.1 grams of morpholine are heated at the boil under reflux for 2¼ hours. Concentrating to dryness in vacuo is then carried out and evaporation with toluene in vacuo is carried out several times. The oily distillation residue (free base) is dissolved in 50 ml of ethanol, and the mixture is adjusted to a pH-value of 4 by the dropwise addition of concentrated hydrochloric acid and then evaporated to dryness in vacuo. By evaporation in vacuo with toluene several times, the distillation residue is dried, and then recrystallised from a small amount of ethanol and ether and again from ethanol.

There were obtained 12.9 grams of [D,L]-3-[2-(3-morpholino-2-hydroxy-propoxy)-phenyl]-crotonic acid nitrile hydrochloride melting at 184.5°–185° C.

EXAMPLE 2

[D,L]-3-[2-(3-N-Phenyl-piperazino-2-hydroxy-propoxy)-phenyl]-crotonic acid nitrile hydrochloride 15 Grams of [D,L]-3-[2-(2,3-Oxido-propoxy)-phenyl]-crotonic acid nitrile in 90 ml of ethanol and 11.4 grams of N-phenylpiperazine are boiled under reflux for 1½ hours. Working up and conversion into the hydrochloride are then carried out as described in Example 1.

There were obtained 14.0 grams of [D,L]-3-[2-(3-N-phenyl-piperazino-2-hydroxy-propoxy)-phenyl]-crotonic acid nitrile hydrochloride melting at 177°-178° C.

EXAMPLE 3

[D,L]-3-[2-(3-2*,6*-Dimethylpiperidino-2-hydroxy-propoxy)-phenyl]-crotonic acid nitrile hydrochloride.

15 Grams of [D,L]-3-[2-(2,3-oxido-propoxy)-phenyl]-crotonic acid nitrile in a mixture of 90 ml of ethanol and 8.0 grams of 2,6-dimethylpiperidine are boiled under reflux for 13 hours, and working up and conversion into the hydrochloride are carried out as described in Example 1.

There were obtained 12.4 grams of [D,L]-3-[2-(3-2*,6*-dimethylpiperidino-2-hydroxy-propoxy)-phenyl]-crotonic acid nitrile hydrochloride melting at 157°-158° C.

EXAMPLE 4

[D,L]-3-[2-(3-3*,4*-dimethoxyphenethylamino-2-hydroxy-propoxy)-phenyl]-crotonic acid nitrile hydrochloride.

19 Grams of [D,L]-3-[2-(2,3-Oxido-propoxy)-phenyl]-crotonic acid nitrile in a mixture of 100 ml of ethanol and 12.7 grams of homoveratrylamine are boiled under reflux for 5 hours. Working up and conversion into the hydrochloride are then carried out as described in Example 1.

There were obtained 10.8 grams of [D,L]-3-[2-(3-3*,4*-dimethoxyphenethylamino-2-hydroxy-propoxy)-phenyl]-crotonic acid nitrile hydrochloride melting at 164°-165° C.

The free base is isolated from the mother liquor in the usual manner (rendering alkaline, extracting with toluene, concentrating to dryness in vacuo) and there were obtained by recrystallisation from toluene/diisopropyl ether 1.2 grams thereof melting at 88° to 89° C.

EXAMPLE 5

[D,L]-3-[2-(3-N-[2*]-Pyridino-piperazino-2-hydroxy-propoxy)-phenyl]-crotonic acid nitrile trihydrochloride.

7 Grams of [D,L]-3-[2-(2,3-oxide-propoxy)-phenyl]-crotonic acid nitrile in a mixture of 70 ml of ethanol and 6 grams of N-(2-pyridino)-piperazine are boiled under reflux for 3 hours. Working up and conversion into the trihydrochloride is then carried out as described in Example 1. 5.1 Grams of [D,L]-3-[2-(3-N-[2*]-pyridino-piperazino-2-hydroxy-propoxy)-phenyl]-crotonic acid nitrile trihydrochloride melting at 121° C. are obtained.

EXAMPLE 6

[D,L]-3-[2-(3-N-[4-Acetylphenyl]-piperazino-2-hydroxy-propoxy)-phenyl]-crotonic acid nitrile dihydrochloride.

7 Grams of [D,L]-3-[2-(2,3-oxido-propoxy)-phenyl]-crotonic acid nitrile in a solution of 6.8 grams of N-(4-piperazino)-acetophenone in 70 ml of ethanol are boiled under reflux for 3 hours. Evaporation to dryness in vacuo is then carried out. The oily distillation residue crystallises after a few hours. Trituration with a small amount of ether and filtering off with suction are then carried out. The filter residue was dissolved in exactly the sufficient quantity of chloroform, and a saturated solution of hydrochloric acid/chloroform is added in portions, while stirring, until the reaction is acid. After a short time the dihydrochloride separates from the clear solution.

By filtering off with suction, washing with a small amount of chloroform/acetone and drying, 9 grams of [D,L]-3-[2-(3-N-[4-acetylphenyl]-piperazino-2-hydroxy-propoxy)-phenyl]-crotonic acid nitrile dihydrochloride melting at 151° C. are obtained.

EXAMPLE 7

[D,L]-3-[2-(3-N[2-Methoxyphenyl]-piperazino-2-hydroxy-propoxy)-phenyl]-crotonic acid nitrile dihydrochloride.

6 Grams of [D,L]-3-[2-(2,3-oxido-propoxy)-phenyl]-crotonic acid nitrile in a solution of 5.5 grams of N-(2-methoxy-phenyl)-piperazine in 60 ml of ethanol are boiled under reflux for 3 hours. Concentration to dryness in vacuo is then carried out, the residue is dissolved in chloroform and the solution is rendered acid with hydrochloric acid/chloroform. Rotation to dryness in vacuo is then carried out, and crystallisation is brought about by trituration with a small amount of ether. By filtering off with suction and drying there are obtained 10.5 grams of [D,L]-3-[2-(3-N-[2-methoxyphenyl]-piperazino-2-hydroxypropoxy)-phenyl]-crotonic acid nitrile dihydrochloride melting at 171° C.

EXAMPLE 8

[D,L]-3-[2-(3-N-[2-Methylphenyl]-piperazino-2-hydroxy-propoxy)-phenyl]-crotonic acid nitrile dihydrochloride, 7 Grams of [D,L]-3-[2-(2,3-oxido-propoxy)-phenyl]-crotonic acid nitrile in a mixture of 6.5 grams of N-(orthotolyl)-piperazine and 70 ml of ethanol are reacted and worked up as described in Example 7.

There are obtained 10 grams of [D,L]-3-[2-(3-N-[2-methylphenyl-7-piperazino-2-hydroxy-propoxy)-phenyl-7-crotonic acid nitrile dihydrochloride melting at 138° C.

EXAMPLE 9

[D,L]-3-[2-(3-N-[Methylpiperazino]-2-hydroxy-propoxy)-phenyl]-crotonic acid nitrile dihydrochloride, 7 Grams of [D,L]-3-[2-(2,3-oxido-propoxy)-phenyl]-crotonic acid nitrile are reacted with 3 grams of N-methylpiperazine in 60 ml of absolute ethanol and worked up, as described in Example 7. The crude dihydrochloride is dissolved in 50 ml of water and filtered over 3 grams of active carbon. The filtrate is concentrated to dryness finally under a high vacuum. The resulting foam is triturated with ether, filtered off with suction and dried.

There are obtained 4.9 grams of strongly hygroscopic [D,L]-3-[2-(3-N-[methylpiperazino]-2-hydroxy-propoxy)-phenyl]-crotonic acid nitrile dihydrochloride.

The compound exhibits in the IR characteristic bands at 2203, 1590, 1435, 1235 and 745 cm$^{-1}$.

EXAMPLE 10

[D,L]-3-[2-(3-N-[2-Hydroxyethyl]-piperazino-2-hydroxy-propoxy)-phenyl]-crotonic acid nitrile dihydrochloride.

7 Grams of [D,L]-3-[2-(2,3-Oxido-propoxy)-phenyl]-crotonic acid nitrile are reacted with 4.7 grams of N-(2-hydroxyethyl)-piperazine in 70 ml of absolute ethanol are reacted and worked up, as described in Example 9.

There are obtained 8.5 grams of [D,L]-3-[2-(3-N-[2-hydroxethyl]-piperazino-2-hydroxy-propoxy)-phenyl]-crotonic acid nitrile dihydrochloride melting at 146° C.

EXAMPLE 11

[D,L]-3-[4-(3-N-Phenylpiperazino-2-hydroxy-propoxy)-phenyl]-crotonic acid nitrile hydrochloride 10.75 Grams of [D,L]-3-[4-(2,3-oxido-propoxy)-phenyl]-crotonic acid nitrile in a solution of 8.1 grams of phenylpiperazine in 60 ml of ethanol are boiled under reflux for 3 hours. The reaction mixture is then cooled with ice and, after standing for a short time, the crystals that separate are filtered off with suction and recrystallised from a small amount of ethanol.

12.9 Grams of the free base melting at 133°–134° C. are obtained. The base is dissolved at room temperature in just the sufficient quantity of acetone, and then concentrated hydrochloric acid is added dropwise, while stirring, until the pH-value is 4.5. After a short time the hydrochloride precipitates. It is filtered off with suction and dried. There are obtained 13.9 grams of crude hydrochloride melting at 158°–160° C.

By recrystallisation once from a large amount of ethanol 13.3 grams of [D,L]-3-[4-(3-N-phenyl-piperazino-2-hydroxypropoxy)-phenyl]-crotonic acid nitrile hydrochloride melting at 160°–161° C., are obtained.

EXAMPLE 12

[D,L]-3-[4-(3-Morpholino-2-hydroxy-propoxy)-phenyl]-crotonic acid nitrile hydrochloride 15.0 Grams of [D,L]-3-[4-(2,3-oxido-propoxy)-phenyl]crotonic acid nitrile in a solution of 6.1 grams of morpholine in 100 ml of ethanol are heated at 80° C. for 4½ hours. The mixture is allowed to stand for a further 12 hours at room temperature. The mixture is then concentrated to dryness in vacuo and evaporated three times with toluene. The distillation residue is dissolved in a small amount of toluene, and caused to crystallise by the addition of diisopropyl ester. By filtering off with suction and drying, 18.0 grams of the free base melting at 79°–80° C. are obtained.

Conversion into the hydrochloride is then carried out as described in Example 1.

There are obtained 16.4 grams of [D,L]-3-[4-(3-morpholino-2-hydroxy-propoxy)-phenyl]-crotonic acid nitrile hydrochloride melting at 121°–122° C.

EXAMPLE 13

[D,L]-3-[4-(3-2*,6*-Dimethylpiperidino-2-hydroxy-propoxy)phenyl]-crotonic acid nitrile hydrochloride.

15 Grams of [D,L]-3-[4-(2,3-oxido-propoxy)-phenyl]-crotonic acid nitrile in a solution of 8.0 grams of 2,6-dimethylpiperidine in 100 ml of ethanol are boiled under reflux for 6½ hours. The mixture is then evaporated to dryness in vacuo, and the distillation residue is dissolved in 80 ml of toluene. After the addition of 300 ml of water, the mixture is adjusted to a pH-value of 4 with concentrated hydrochloric acid with good agitation. To the aqueous phase are added 80 ml of fresh toluene and the pH-value is adjusted to 10 by agitation with sodium hydroxide solution. Extraction is carried out twice with 50 ml of toluene each time, and the combined organic extracts are washed with water, dried over sodium sulphate and concentrated to dryness in vacuo. By trituration with diisopropyl ether, filtering off the resulting crystals with suction and drying there are obtained 15.0 grams of the free base melting at 97°–98° C.

From the latter there are obtained in a manner described in Example 1 14.5 grams of [D,L]-3-[4-(3-2*,6*-dimethylpiperidino-2-hydroxy-propoxy)-phenyl]-crotonic acid nitrile hydrochloride melting at 168°–169° C.

EXAMPLE 14

[D,L]-3-[4-(3-3*,4*-Dimethoxyphenethylamino-2-hydroxy-propoxy)-phenyl]-crotonic acid nitrile hydrochloride.

17.5 grams of [D,L]-3-[4-(2,3-oxido-propoxy)-phenyl]-crotonic acid nitrile in a solution of 15.0 grams of homoveratrylamine in 100 ml of ethanol are heated at the boil under reflux for 5 hours. After the usual working up (see Example 1), the free crude base is recrystallised from ethanol/diisopropyl ether and again from ethanol.

There are obtained 16.1 grams of free base melting at 141.5°–142° C. From the latter there are obtained, in a manner analogous to that in Example 1, 13.6 grams of [D,L]-3-[4-(3-3*,4*-dimethoxyphenethylamino-2-hydroxy-propoxy)-phenyl]-crotonic acid nitrile hydrochloride melting at 148°–149° C.

EXAMPLE 15

[D,L]-3-[4-(3-N-2*-pyridyl-piperazino-2-hydroxy-propoxy)-phenyl]-crotonic acid nitrile dihydrochloride.

10.175 Grams of [D,L]-3-[4-(2,3-oxido-propoxy)-phenyl]-crotonic acid nitrile in a solution of 8.2 grams of pyridyl-piperazine in 60 ml of ethanol are boiled under reflux for 3 hours. The mixture is then cooled with ice, and the precipitated crystals are collected and dried. The resulting 17.1 grams of free base melting at 131°–132° C. are converted in the usual manner into 15.1 grams of [D,L]-3-[4-(3-N-2*-pyridyl-piperazino-2-hydroxy-propoxy)-phenyl]-crotonic acid nitrile dihydrochloride melting at 259°–260° C.

EXAMPLE 16

[D,L]-3-[4-(3-N-4*-Acetyl-phenyl-piperazino-2-hydroxy-propoxy)phenyl]-crotonic acid nitrile hydrochloride.

10.75 Grams of [D,L]-3-[4-(2,3-oxido-propoxy)-phenyl]-crotonic acid nitrile are boiled under reflux in a solution of 10.2 grams of para-piperazinoacetophenone for 4 hours. The base, obtained by cooling, crystallising, filtering off with suction and drying (20.1 grams, melting at 160°–161° C.) is adjusted in 100 ml of absolute ethanol and 30 ml of dimethylformamide with concentrated hydrochloric acid to a pH-value of 5. The hydrochloride that crystallises out is collected and recrystallised hot from ethanol/water.

There are obtained 17.7 grams of [D,L]-3-[4-(3-N-4*-acetyl-phenyl-piperazino-2-hydroxy-propoxy)-phenyl]-crotonic acid nitrile hydrochloride melting at 221°–222° C.

EXAMPLE 17

**[D,L]-3-[4-(3-N-2*-Methoxy-phenylpiperazino-2-hydroxy-propoxy)-phenyl]-crotonic acid nitrile hydrochloride.**

10.75 Grams of [D,L]-3-[4-(2,3-oxido-propoxy)-phenyl]-crotonic acid nitrile are boiled under reflux for 5 hours in a solution of 10.3 grams of N-(2-methoxy-phenyl)-piperazine dihydrochloride in a mixture of 14.0 ml of triethylamine and 60 ml of ethanol. Concentration to dryness is then carried out in vacuo, and the crude base is caused to crystallise by the addition of ethanol. By filtering off with suction, subsequently washing with ethanol and water there are obtained, after drying, 15.0 grams of free base melting at 102°–103° C. It is then converted in the usual manner (see Example 1) into the hydrochloride. By recrystallisation twice from ethanol there are obtained 13.3 grams of [D,L]-3-[4-(3-N-2*-methoxy-phenylpiperazino-2-hydroxy-propoxy)-phenyl]crotonic acid nitrile hydrochloride melting at 198°–199° C.

EXAMPLE 18

**[D,L]-3-[4-(3-N-2*-Methyl-phenyl-piperazino-2-hydroxy-propoxy)-phenyl]-crotonic acid nitrile hydrochloride.**

10.95 Grams of [D,L]-3-[4-(2,3-oxido-propoxy)-phenyl]-crotonic acid nitrile are boiled under reflux for 3 hours in a solution of 8.8 grams of ortho-tolyl-piperazine. After cooling, 16.5 grams of the free base crystallise out, melting at 104°–105° C. It is converted into the hydrochloride as described in Example 1. By finally recrystallising twice from ethanol there are obtained 10.0 grams of [D,L]-3-[4-(3-N-2*-methylphenyl-piperazino-2-hydroxy-propoxy)phenyl]-crotonic acid nitrile hydrochloride melting at 233°–234° C.

EXAMPLE 19

**[D,L]-3-[4-(3-N-3*-Methyl-phenyl-piperazino-2-hydroxy-propoxy)-phenyl]-crotonic acid nitrile hydrochloride.**

10.75 Grams of [D,L]-3-[4-(2,3-oxido-propoxy)-phenyl]-crotonic acid nitrile are reacted as described in Example 17 with 8.8 grams of meta-tolyl-piperazine.

By working up in the same manner there are obtained from 16.4 grams of the free base melting at 108°–109° C., 14.6 grams of [D,L]-3-[4-(3-N-3*-methyl-phenyl-piperazino-2-hydroxy-propoxy)-phenyl]-crotonic acid nitrile hydrochloride melting at 151°–152° C.

EXAMPLE 20

[D,L]-3-[4-(3-N-Methyl-piperazino-2-hydroxy-propoxy)-phenyl]crotonic acid nitrile dihydrochloride.

10.75 Grams of [D,L]-3-[4-(2,3-oxido-propoxy)-phenyl]-crotonic acid nitrile are reacted as described in Example 17 with 5.0 grams of N-methylpiperazine in 60 ml of ethanol, and, as described in Example 1, worked up and converted into the dihydrochloride.

There are obtained 11.8 grams of [D,L]-3-[4-(3-N-methyl-piperazino-2-hydroxy-propoxy)-phenyl]-crotonic acid nitrile dihydrochloride melting at 217°–218° C.

EXAMPLE 21

**[D,L]-3-[4-(3-N-2*-oxyethyl-piperazino-2-hydroxy-propoxy)phenyl]-crotonic acid nitrile dihydrochloride.**

5.0 Grams of [D,L]-3-[4-(2,3-oxido-propoxy)-phenyl]-crotonic acid nitrile are boiled under reflux for 2 hours in a solution of 3.5 grams of hydroxyethyl-piperazine in 50 ml of ethanol. After evaporation to dryness in vacuo, crystallisation from toluene is carried out. The resulting 5.7 grams of free base melting at 101°–102° C. are converted as described in Example 1 into 6.7 grams of [D,L]-3-[4-(3-N-2*-oxyethyl-piperazino-2-hydroxy-propoxy)-phenyl]-crotonic acid nitrile dihydrochloride melting at 204°–205° C.

EXAMPLE 22

**[D,L]-3-[2-(3-3A*,4*-Dimethoxy-phenethylamino-2-hydroxy-propoxy)-phenyl]-acrylic acid tert.-butyl ester hydrochloride.**

30.0 Grams of [D,L]-3-[2-(2,3-oxido-propoxy)-phenyl]-acrylic acid tert.-butyl ester are heated at the boil under reflux for 2 hours in a solution of 20.0 grams of homoveratrylamine in 60 ml of ethanol. After working up in the usual manner (see Example 1), 15.9 grams of [D,L]-3-[2-(3-3*,4*-dimethoxy-phenethylamino-2-hydroxy-propoxy)-phenyl]-acrylic acid tert.-butyl ester hydrochloride melting at 167°–168° C. are obtained.

EXAMPLE 23

**[D,L]-3-[2-(3-N-2*-oxyethyl-piperazino-2-hydroxy-propoxy)-phenyl]-acrylic acid tert.-butyl ester dihydrochloride.**

11.0 Grams of [D,L]-3-[2-(2,3-oxidopropoxy)-phenyl]-acrylic acid tert.-butyl ester are boiled under reflux for 2 hours in a mixture of 55 grams of N-hydroxyethyl-piperazine and 60 ml of ethanol. Working up is then carried out as in Example 12, but in this case the pH-value is 3 instead of 4. 6.4 Grams of [D,L]-3-[2-(3-N-2*-oxyethyl-piperazino-2-hydroxy-propoxy)-phenyl]-acrylic acid tert.-butylester dihydrochloride melting at 168° C. (with decomposition) are obtained.

EXAMPLE 24

[D,L]-3-[2-(3-N-phenylpiperazino-2-hydroxy-propoxy)-phenyl]-acrylic acid tert.-butyl ester hydrochloride.

11.0 Grams of [D,L]-3-[2-(2,3-oxidopropoxy)-phenyl]-acrylic acid tert.-butyl ester are boiled under reflux for one hour in a mixture of 6.5 grams of phenyl-piperazine and 50 ml of ethanol, and working up is carried out as described in Example 1. In this case the hydrochloride is finally recrystallised twice from ethanol. 6.2 Grams of [D,L]-3-[2-(3-N-phenylpiperazino-2-hydroxy-propoxy)-phenyl]-acrylic acid tert.-butyl ester hydrochloride melting at 200°–201° C. (with decomposition) are obtained.

EXAMPLE 25

**[D,L]-3-[4-(3-3*,4AA*-Dimethoxyphenethylamino-2-hydroxy-propoxy)-phenyl]-acrylic acid tert.-butyl ester hydrochloride.**

15.0 Grams of [D,L]-3-[4-(2,3-oxidopropoxy)-phenyl]-acrylic acid tert.-butyl ester are boiled under reflux for 8 hours in a solution of 10.5 grams of homoveratrylamine. Working up is carried out in the usual manner, and the crude hydrochloride is dissolved in 6 liters of water, extracted several times with toluene and the aqueous phase is adjusted to a pH-value of 9 with sodium hydroxide solution. The mixture is then extracted with toluene and ethyl acetate. The combined organic extracts are evaporated to dryness in vacuo, and crystallisation is caused with diisopropyl ether. 6.95 Grams of free base are obtained melting at 100°–101° C. From the latter are obtained as described in Example 1 7.4 grams of [D,L]-3-[4-(3-3*,4*-dimethoxyphenethylamino-2hydroxy-propoxy)-phenyl]-acrylic acid tert.-butyl ester hydrochloride melting at 176°–177° C., which was finally recrystallised twice from ethanol.

EXAMPLE 26

[D,L]-3-Phenyl-3-[2-(3-3*,4*-Dimethoxyphenethylamino-2-hydroxy-propoxy)-phenyl]-acrylic acid nitrile semi-oxalate.

5.4 Grams of [D,L]-3-phenyl-3-[2-(2,3-oxidopropoxy)phenyl]-acrylic acid nitrile are boiled under reflux for 3 hours in a solution of 3.7 grams of homoveratrylamine in 50 ml of ethanol. Working up is then carried out as described in Example 1. The oily free base is then converted as described in Example 28 into the oxalate, but in this case it is adjusted to a pH-value of 6.5 by the addition of oxalic acid. The crude semi-oxalate is again recrystallised twice from ethanol, and 4.1 grams of [D,L]-3-phenyl-3-[2-(3-3*,4*-dimethoxyphenethylamino-2-hydroxy-propoxy)-phenyl]-acrylic acid nitrile semioxalate melting at 172°–173° C. are obtained.

EXAMPLE 27

[D,L]-3-Phenyl-3-[2-(3-N-phenylpiperaazino-2-hydroxy-propoxy)-phenyl]-acrylic acid nitrile hydrochloride.

6.0 grams of [D,L]-3-phenyl-3-[2-(2,3-oxidopropoxy)phenyl]-acrylic acid nitrile are boiled under reflux for 2 hours in a solution of 3.5 grams of phenyl-piperazine in 50 ml of ethanol. The mixture is then concentrated to dryness in vacuo, the distillation residue is evaporated twice with toluene (in vacuo).

The free base was purified by crystallization with toluene/diisopropyl ether. 4.1 Grams melting at 102°–103° C. are obtained. The free base is again as described in Example 1 converted into the hydrochloride. There are obtained 4.4 grams having the double melting point 85° C./184° C.

EXAMPLE 28

[D,L]-3-Phenyl-3-[4-(3-3*,4*-Dimethoxy-phenethylamino-2-hydroxy-propoxy)-phenyl]-acrylic acid nitrile oxalate.

10.0 Grams of [D,L]-3-phenyl-3-[4-(2,3-oxidopropoxy)-phenyl]-acrylic acid nitrile are boiled under reflux for 2 hours in a mixture of 6.5 ml of homoveratrylamine and 50 ml of ethanol. Working up is then carried out as described in Example 25. The crude base is taken up in ethanol, and the mixture is adjusted to a pH-value of 4 with a concentrated solution of oxalic acid in ethanol. By filtering of with suction and drying, 4.9 grams of [D,L]-3-phenyl-3-[4-(3-3*,4*-dimethoxyphenethylamino-2-hydroxy-propoxy)-phenyl]-acrylic acid nitrile oxalate melting at 124°–125° C. are obtained.

EXAMPLE 29

[D,L]-3-Phenyl-3-[4-(3-N-phenylpiperazino-2-hydroxy-propoxy)-phenyl]-acrylic acid nitrile dihydrochloride.

10.0 Grams of [D,L]-3-phenyl-3-[4-(2,3-oxidopropoxy)-phenyl]-acrylic acid nitrile are boiled under reflux for 2 hours in a solution of 5.9 grams of phenyl-piperazine in 50 ml of ethanol. By working up in a manner analogous to that in Example 1, 6.8 grams of [D,L]-3-phenyl-3-[4-(3-N-phenylpiperazino-2-hydroxy-propoxy)-phenyl]-acrylic acid nitrile dihydrochloride melting at 189°–190° C. are obtained.

EXAMPLE 30

[D,L]-3-Phenyl-3-[4-(3-N-[2-hydroxyethyl]-piperazino-2-hydroxy-propoxy)-phenyl]-acrylic acid nitrile dihydrochloride.

In a manner analogous to that in Example 25, 10.0 grams of [D,L]-3-phenyl-3-[4-(2,3-oxido-propoxy)-phenyl]-acrylic acid nitrile are reacted with 4.7 grams of N-hydroxyethylpiperazine in 50 ml of ethanol and worked up. 9.8 Grams of [D,L]-3-phenyl-3-[4-(3-N-[2-hydroxyethyl]-piperazino-2-hydroxy-propoxy)-phenyl]-acrylic acid nitrile dihydrochloride melting at 164°–165° C. are obtained.

EXAMPLE 31

[D,L]-3-[4-(3-3*,4*-Dimethoxyphenethylamino-2-hydroxy-propoxy)-phenyl]-acrylic acid methyl ester hydrochloride.

6 Grams of [D,L]-3-[4-(2,3-oxido-propoxy)-phenyl]-acrylic acid methyl ester are boiled under reflux for 2½ hours in a solution of 4.7 grams of homoveratrylamine in 60 ml of absolute ethanol, and then working up is carried out as described in Example 1. 6.2 Grams of [D,L]-3-[4-(3-3*,4*-dimethoxyphenethylamino-2-hydroxy-propoxy)-phenyl]acrylic acid methyl ester hydrochloride melting at 162° C. are obtained.

EXAMPLE 32

[D,L]-3-[4-(3-N-2*-Methoxyphenyl-piperazino-2-hydroxy-propoxy)-phenyl]-acrylic acid methyl ester dihydrochloride 4.5 Grams of [D,L]-3-[4-(2,3-oxido-propoxy)-phenyl]-acrylic acid methyl ester are boiled under reflux for 3 hours in a solution of 4.0 grams of N-(2-methoxy-phenyl)-piperazine in 60 ml of absolute ethanol. By the usual working up (see Example 1), 6.05 grams of [D,L]-3-[4-(3-N-2*-methoxy-phenyl-piperazino-2-hydroxy-propoxy)-phenyl]-acrylic acid methyl ester dihydrochloride melting at 204° C. are obtained.

EXAMPLE 33

[D,L]-3-[2-(3-3*,4*-Dimethoxy-phenethylamino-2-hydroxy-propoxy)phenyl]-acrylic acid ethyl ester hydrochloride 10.0 Grams of [D,L]-3-[2-(2,3-oxido-propoxy)-phenyl]-acrylic acid ethyl ester are boiled under reflux for 4 hours in a solution of 7.3 grams of homoveratrylamine in 60 ml of ethanol. The mixture is then concentrated to dryness in vacuo. By digestion with hexane the oily distillation residue is caused to crystallise. After filtering off and drying, 9.8 grams of free base melting at 80°–82° C. are obtained. From the latter, the hydrochloride is prepared as described in Example 1 the, which is once again recrystallised from ethanol/water and finally from isopropanol. 8.1 Grams of [D,L]-3-[2-(3-3*,4*-dimethoxy-phenethylamino-2-hydroxy-propoxy)-phenyl]-acrylic acid ethyl ester hydrochloride melting at 161°–162° C. are obtained.

EXAMPLE 34

[D,L]-3-[2-(3-N-phenylpiperazino-2-hydroxy-propoxy)-phenyl]-acrylic acid ethyl ester hydrochloride 10.0 Grams of [D,L]-3-[2-(2,3-oxido-propoxy)-phenyl]-acrylic acid ethyl ester are boiled for 4½ hours in a solution of 6.54 grams of N-phenyl-piperazine in 60 ml of ethanol. Then, as described in Example 1, working up and conversion into the hydrochloride are carried out. The hydrochloride so obtained is finally recrystallised again once from isopropanol and then from ethanol/water. 10.2 Grams of [D,L]-3-[2-(3-N-phenyl-piperazino-2-hydroxy-propoxy)-phenyl]-acrylic acid ethyl ester hydrochloride melting at 186°–187° C. are obtained.

EXAMPLE 35

[D,L]-3-[4-(3-3*,4*-Dimethoxy-phenethylamino-2-hydroxy-propoxy)-phenyl]-3-ethyl-acrylic acid nitrile hydrochloride 15.0 Grams of [D,L]-3-[4-(2,3-oxido-propoxy)-phenyl]-3-ethyl-acrylic acid nitrile are boiled for 2 hours in a solution of 12.0 grams of homoveratrylamine in 100 ml of ethanol, and working up is carried out as described in Example 27. There are obtained first 10.3 grams of the free base melting at 103°–104° C. From the latter are obtained as described in Example 1, 7.5 grams of [D,L]-3-[4-(3-3*,4*-dimethoxy-phenethylamino-2-hydroxy-propoxy)-phenyl]-3-ethyl-acrylic acid nitrile hydrochloride melting at 120°–121° C.

EXAMPLE 36

[D,L]-3-[4-(3-N-Phenyl-piperazino-2-hydroxy-propoxy)-phenyl]-3-ethyl-acrylic acid nitrile dihydrochloride 10.0 Grams of [D,L]-3-[4-(2,3-oxido-propoxy)-phenyl]-3-ethyl-acrylic acid nitrile are boiled under reflux for 2 hours in a solution of 11.0 grams of phenyl-piperazine in 50 ml of ethanol. The reaction mixture is then cooled to 5° C., and the free base crystallises out. 8.2 Grams of the free base melting at 110°–115° C. are obtained, from which there are obtained, as described in Example 1 by means of 4.19 ml of 10 N-hydrochloric acid, 8.1 grams of [D,L]-3-[4-(3-N-phenyl-piperazino-2-hydroxy-propoxy)-phenyl]-3-ethyl-acrylic acid nitrile dihydrochloride melting at 202°–204° C.

EXAMPLE 37

[D,L]-3-[4-(3-N-[2-Hydroxyethyl]-piperazino-2-hydroxy-propoxy)-phenyl]-3-ethyl-acrylic acid nitrile dihydrochloride 10.0 Grams of [D,L]-3-[4-(2,3-oxido-propoxy)-phenyl]-3-ethyl acrylic acid nitrile in a solution of 6.0 grams of N-hydroxyethyl-piperazine are reacted and worked up as in Example 25 (2.0 liters of water). There are obtained first 6.4 grams of the free base melting at 80°–81° C. and therefrom by means of 3.57 ml of 10 N-hydrochloric acid, 7.2 grams of [D,L]-3-[4-(3-N-[2-hydroxyethyl]-piperazino-2-hydroxy-propoxy)-phenyl]-3-ethyl-acrylic acid nitrile dihydrochloride melting at 181°–182° C.

EXAMPLE 38

[D,L]-3-[2-(3-3*,4*-Dimethoxy-phenethylamino-2-hydroxy-propoxy)phenyl]-3-ethyl-acrylic acid methyl ester hydrochloride 8 Grams of [D,L]-3-[2-(2,3-oxidopropoxy)-phenyl]-3-ethyl-acrylic acid methyl ester hydrochloride are boiled under reflux for 3 hours in a solution of 5.7 grams of homoveratrylamine in 80 ml of absolute ethanol. Working up is then carried out as described in Example 1. 4.3 Grams of [D,L]-3-[2-(3-3*,4*-dimethoxy-phenethylamino-2-hydroxy-propoxy)-phenyl]-3-ethyl-acrylic acid methyl ester hydrochloride are obtained. The free base shows characteristic IR-bands at 2920, 1710, 1630, 1585, 1505, 1437, 1225, 1145, 1015, 798 and 748 cm$^{-1}$.

EXAMPLE 39

[D,L]-3-[2-(3-N-2*-Methoxy-phenyl-piperazino-2-hydroxy-propoxy)-phenyl]-3-ethyl-acrylic acid methyl ester dihydrochloride 8 Grams of [D,L]-3-[2-(2,3-oxido-propoxy)-phenyl]-3-ethyl-acrylic acid methyl ester are reacted, as described in Example 32, with a solution of 6.8 grams of N-(2-methoxy-phenyl)-piperazine in 80 ml of absolute ethanol, and worked up. 4.4 Grams of [D,L]-3-[2-(3-N-2*-methoxy-phenyl-piperazino-2-hydroxy-propoxy)-phenyl]-3-ethyl-acrylic acid methyl ester dihydrochloride melting at 120°–122° C. are obtained.

EXAMPLE 40

[D,L]-3-[2-(3-3*,4*-Dimethoxy-phenethylamino-2-hydroxy-propoxy)-phenyl]-crotonic acid ethyl ester oxalate.

12.0 Grams of [D,L]-3-[2-(2,3-oxido-propoxy)-phenyl]-crotonic acid ethyl ester are stirred for 16 hours at 20° to 25° C. in a solution of 7.2 grams of homoveratrylamine in 100 ml of ethanol, and then working up is carried out as described in Example 28. 4.5 Grams of [D,L]-3-[2-(3-3*,4*-dimethoxy-phenethylamino-2-hydroxy-propoxy)-phenyl]-crotonic acid ethyl ester oxalate melting at 115°–117° C. (with decomposition) are obtained.

EXAMPLE 41

[D,L]-3-[2-(3-N-2*-Methoxy-phenylpiperazino-2-hydroxy-propoxy)-phenyl]-crotonic acid ethyl ester dihydrochloride.

7.9 Grams of [D,L]-3-[2-(2,3-oxido-propoxy)-phenyl]-crotonic acid ethyl ester are stirred at room temperature for 48 hours in a solution of 5.8 grams of N-2-methoxy-phenylpiperazine in 100 ml of ethanol. Then working up to the crude base is then carried out as described in Example 1. It is dissolved in a small amount of ethyl acetate and chromatographed over a column of 240 grams of silica gel (Silica gel 60, Merck). Finally, elution with ethyl acetate yielded 4.4 grams of purified base in the form of an oil. It is then converted in the usual manner (see Example 1) into 2.9 grams of [D,L]-3-[2-(3-N-2*-methoxy-phenylpiperazino-2-hydroxy-propoxy)-phenyl]-crotonic acid ethyl ester dihydrochloride melting at 134°–136° C.

EXAMPLE 42

[D,L]-3-[3-(3-N-2*-Methoxy-phenyl-piperazino-2-hydroxy-propoxy)-phenyl]-acrylic acid nitrile dihydrochloride 12.0 Grams of [D,L]-3-[3-(2,3-oxido-propoxy)-phenyl]-acrylic acid nitrile are boiled under reflux for one hour in a solution of 11.5 grams of N-2-methoxy-phenylpiperazine in 50 ml of ethanol. Then working up is carried out in a manner analogous to that in Example 25 (but in this case using 4 liters of water and using soda solution instead of NaOH). The crude free base is oily and is converted as described in Example 1 into 15.7 grams of [D,L]-3-[3-(3-N-2*-methoxy-phenyl-piperazino-2-hydroxy-propoxy)-phenyl]-acrylic acid nitrile dihydrochloride melting at 210° C. (with decomposition).

EXAMPLE 43

[D,L]-3-[3-(3-N-[2-Hydroxyethyl]-piperazino-2-hydroxy-propoxy)-phenyl]-acrylic acid nitrile dihydrochloride.

12.0 Grams of [D,L]-3-[3-(2,3-oxido-propoxy)-phenyl]-acrylic acid nitrile are, as described in Example 42, reacted with 20.0 grams of N-2-hydroxy-ethylpiperazine in 50 ml of ethanol and worked up. 13.5 Grams of [D,L]-3-[3-(3-N-[2-hydroxyethyl]-piperazino-2-hydroxy-propoxy)-phenyl]-acrylic acid nitrile dihydrochloride melting at 180°–182° C. are obtained.

EXAMPLE 44

[D,L]-3-[3-(3-3*,4*-dimethoxyphenethylamino-2-hydroxy-propoxy)-phenyl]-acrylic acid nitrile hydrochloride.

12.0 Grams of [D,L]-3-[3-2,3-oxido-propoxy)-phenyl]-acrylic acid nitrile are reacted as in Example 42 with 10.8 grams of homoveratrylamin in 50 ml of ethanol, and worked up to 6.8 grams of [D,L]-3-[3-(3-3*,4*-dimethoxyphenethylamino-2-hydroxy-propoxy)-phenyl]-acrylic acid nitrile hydrochloride melting at 113°–114° C.

EXAMPLE 45

[D,L]-3-[3-3*,4*-Dimethoxy-phenethylamino-2-hydroxy-propoxy)-phenyl]-acrylic acid ethyl ester hydrochloride 6.0 Grams of [D,L]-3-[3-(2,3-oxido-propoxy)-phenyl]-acrylic acid ethyl ester are stirred for 16 hours at room temperature in a solution of 3.6 grams of homoveratrylamine in 30 ml of ethanol, and then worked up to the crude base as described in Example 28. The latter is reacted as described in Example 1 to yield 3.6 grams of [D,L]-3-[3-(3-3*,4*-dimethoxy-phenethylamino-2-hydroxy-propoxy)-phenyl]-acrylic acid ethyl ester melting at 128°–129° C.

EXAMPLE 46

[D,L]-3-[3-(3-N-2*-Methoxyphenyl-piperazino-2-hydroxy-propoxy)-phenyl]-acrylic acid ethyl ester dihydrochloride 6.0 Grams of [D,L]-3-[3-(2,3-oxido-propoxy)-phenyl]-acrylic acid ethyl ester are stirred for 48 hours at room temperature in a solution of 3.9 grams of N-2-methoxy-phenylpiperazine. By working up in a manner analogous to that in Example 1, 3.4 grams of [D,L]-3-[3-(3-N-2*-methoxyphenyl-piperazino-2-hydroxy-propoxy)-phenyl]-acrylic acid ethyl ester dihydrochloride melting at 164°–165° C. are obtained.

EXAMPLE 47

[D,L]-3-[3-(3-N-[2-Hydroxyethyl]-piperazino-2-hydroxy-propoxy)-phenyl]-acrylic acid ethyl ester dihydrochloride 12.0 Grams of [D,L]-3-[3-(2,3-oxido-propoxy)-phenyl]-acrylic acid ethyl ester are stirred for 48 hours at 20° to 24° C. in a solution of N-2-hydroxyethyl-piperazine in 60 ml of ethanol. By working up in a manner analogous to that in Example 45, 9.3 grams of [D,L]-3-[3-(3-N-[2-hydroxyethyl]-piperazino-2-hydroxy-propoxy)-phenyl]-acrylic acid ethyl ester dihydrochloride melting at 189°–190° C. are obtained.

EXAMPLE 48

[D,L]-3-[Phenyl-3-[4-(3-N-2*-methoxyphenyl-piperazino-2-hydroxy-propoxy)-phenyl]-acrylic acid methyl ester dihydrochloride.

15.0 Grams of [D,L]-2-phenyl-3-[4-(2,3-oxido-propoxy)-phenyl]-acrylic acid methyl ester are stirred for 16 hours at 20° to 24° C. in a solution of 9.3 grams of N-2-methoxyphenyl-piperazine in 150 ml of methanol. Working up to the free base is carried out as described in Example 25. The purified base obtained as an oil is converted into the hydrochloride as described in Example 1. By recrystallisation from methanol/ether and finally from methanol, 13.8 grams of [D,L]-2-phenyl-3-[4-(3-N-2*-methoxyphenyl-piperazino-2-hydroxy-propoxy)-phenyl]-acrylic acid methyl ester dihydrochloride melting at 168°–170° C. (with decomposition) are obtained.

EXAMPLE 49

[D,L]-3-Phenyl-3-[4-(3-N-[2-hydroxyethyl]-piperazino-2-hydroxy-propoxy)-phenyl]-acrylic acid methyl ester dihydrochloride.

15.0 Grams of [D,L]-2-phenyl-3-[4-(2,3-oxido-propoxy)-phenyl]-acrylic acid methyl ester are reacted as described in Example 48 with 6.3 grams of N-2-hydroxyethyl-piperazine in 150 ml of methanol and worked up. 16.4 grams of [D,L]-2-phenyl-3-[4-(3-N-[2-hydroxyethyl]-piperazino-2-hydroxy-propoxy)-phenyl]-acrylic acid methyl ester dihydrochloride melting at 218°–220° C. are obtained.

EXAMPLE 50

[D,L]-3-Phenyl-3-[4-(3-3*,4*-Dimethoxyphenethylamino-2-hydroxy-propoxy)-phenyl]-acrylic acid methyl ester.

15 Grams of [D,L]-2-phenyl-3-[4-(2,3-oxido-propoxy)-phenyl]-acrylic acid methyl ester are stirred at room temperature for 24 hours in a solution of 8.22 grams of homoveratrylamine. The crude hydrochloride obtained in a manner analogous to that in Example 1, this time by adjusting the pH value to 6, is recrystallised first from isopropanol/diisopropyl ether and finally from toluene/methylene chloride. 4.1 Grams of [D,L]-2-phenyl-3-[4-(3-3*,4*-dimethoxyphenethylamino-2-hydroxy-propoxy)-phenyl]-acrylic acid methyl ester melting at 145°–147° C. are obtained.

EXAMPLE 51

[D,L]-3-[3-(3-3*,4*-Dimethoxyphenethylamino-2-hydroxy-propoxy)-phenyl]-crotonic acid nitrile hydrochloride 15 Grams of [D,L]-3-[3-(2,3-oxido-propoxy)-phenyl]-crotonic acid nitrile are boiled under reflux for 2½ hours in a solution of 12.62 grams of homoveratrylamine in 150 ml of ethanol, and worked up as described in Example 25. The oily free base so purified is finally converted, as described in Example 1, into 6.5 grams of pure [D,L]-3-[3-(3-3*,4*-dimethoxyphenethylamino-2-hydroxy-propoxy)-phenyl]-crotonic acid nitrile hydrochloride melting at 135°–138° C.

EXAMPLE 52

[D,L]-3-[3-(3-N-2*-Methoxyphenyl-piperazino-2-hydroxy-propoxy)phenyl]-crotonic acid nitrile hydrochloride 15 Grams of [D,L]-3-[3-(2,3-oxido-propoxy)-phenyl]-crotonic acid nitrile are boiled uner reflux for 1½ hours in a solution of 3.9 grams of N-2-methoxy-phenylpiperazine in 150 ml of ethanol. By working up in a manner analogous to that in Example 1, 17.1 grams of [D,L]-3-[3-(3-N-2*-methoxyphenyl-piperazino-2-hydroxy-propoxy)-phenyl]-crotonic acid nitrile hydrochloride melting at 160°–162° C. are obtained.

EXAMPLE 53

[−]- and [+]-3-[4-(3-3*,4*-Dimethoxyphenethylamino-2-hydroxy-propoxy)-phenyl]-crotonic acid nitrile hydrochloride A solution of 50 grams of [D,L]-3-[4-(3-3*,4*-dimethoxy-phenethyl-amino-2-hydroxy-propoxy)-phenyl]-crotonic acid nitrile in 200 ml of ethanol is mixed with a solution of 19.2 grams of D-(−)-mandelic acid in 150 ml of ethanol. After standing for a short time, the crystals that separate are filtered off with suction. By washing with a small amount of ethanol and drying in vacuo, there are isolated 32.8 grams of [−]-3-[4-(3-3*,4*-dimethoxyphenethylamino-2-hydroxy-propoxy)-phenyl]-crotonic acid nitrile-D-9-)-mandelate melting at 114°–116° C. which issparingly soluble in ethanol, $[\alpha]^D = -35.4°$ (c=0.6, methanol). By recrystallisation from 200 ml of hot ethanol, 28.9 grams of the pure mandelate are obtained melting at 118°–119° C. and having a rotation value of $[\alpha]^D = -38.2°$ (c=0.6, methanol), yield 83.5%.

A mixture of 3.15 ml of concentrated aqueous ammonia solution with 30 ml of water is added dropwise, while cooling with ice, to a rapidly-stirred mixture of 23 grams of the above laevo-rotatory mandelate, 230 ml of water, and 100 ml of chloroform. The organic phase is separated, washed with some water, and, after being dried over sodium sulphate, is concentrated to dryness in vacuo.

From the resulting (−)-3-[4-(3-3*,4*-dimethoxyphenethylamino-2-hydroxy-propoxy)-phenyl]-crotonic acid nitrile, the hydrochloride described in Example 1 is obtained, which, after recrystallisation from ethanol/ether, melts at 166°–167° C. and has a rotation value of $[\alpha]^D = -12.8°$ (c=0.5 methanol), final yield 17.5 grams (96.4%).

By evaporation of the ethanolic mother liquors of the above racemate splitting, there is obtained the [+]-3-[4-(3-3*,4*-dimethoxyphenethylamino-2-hydroxy-propoxy)-phenyl]-crotonic acid nitrile-D-(−)-mandelate, which is very readily soluble in ethanol. From the latter the [+]-3-[4-(3-3*,4*-dimethoxyphenethylamino-2-hydroxy-propoxy)-phenyl]-crotonic acid nitrile can be prepared as described above. By recrystallisation from toluene/petroleum ether 25.4 grams of the nitrile melting at 132°–135° C. are obtained. The latter, as in the case of the (−)-antipodes already described, is converted into the dextro-rotatory hydrochloride. By recrystallisation from ethanol/ether, there are obtained 15.5 grams (96%) of not quite optically pure [+]-3-[4-(3-3*,4*-dimethoxyphenethylamino-2-hydroxy-propoxy)-phenyl]-crotonic acid nitrile hydrochloride melting at 162°–164° C. having a rotational value of $\alpha^D = +9.7°$ (c=0.6, methanol).

EXAMPLE 54

[D,L]-3-[3-fluoro-4-(3-3*,4*-dimethoxyphenethylamino-2-hydroxy-propoxy)-phenyl]-crotonic acid nitrile hydrochloride 10.0 Grams of [D,L]-3-[3-fluoro-4-(2,3-oxido-propoxy)-phenyl]-crotonic acid nitrile are boiled under reflux for 3½ hours in a mixture of 10.0 grams of homoveratrylamine and 20 ml of ethanol. For further purification the crude hydrochloride obtained as described in Example 1 is dissolved in 5 l of water and extracted with toluene/ethyl acetate/ether to remove neutral constituents. Then, the reaction mixture is rendered weakly alkaline by the addition of sodium bicarbonate and extracted with toluene/ethyl acetate. After drying and concentrating by evaporation and recrystallization from toluene/ether, the base, 7.9 grams melting at 111° to 112° C., is dissolved in a small amount of ethanol and concentrated hydrochloric acid is added to adjust a pH of 4, whereupon the hydrochloride separates at once in crystal form. 7.3 grams of [D,L]-3-[3-fluoro-4-(3-3*,4*-di-methoxyphenethylamino-2-hydroxy-propoxy)-phenyl]-crotonic acid nitrile hydrochloride melting at 163° to 164° C. are obtained.

EXAMPLE 55

[D,L]-3-[2-(3-N-2*-methoxyphenyl-piperazino-2-hydroxy-propoxy)-5-fluorophenyl]-crotonic acid nitrile hydrochloride 5.7 Grams of N-2-methoxy-phenylpiperazine are added to a solution of 6.5 grams of [D,L]-3-[2-(2,3-oxido-propoxy)-5-fluorophenyl]-crotonic acid nitrile in 30 ml of ethanol and the whole is boiled under reflux for 2 hours. The mixture is cooled and by cautiously adding concentrated hydrochloric acid a pH of 4.0 is adjusted. The crude hydrochloride obtained after the addition of petroleum ether is filtered off with suction and recrystallized from ethanol. 6.2 Grams of [D,L]-3-[2-(3-N-2*-methoxyphenyl-piperazino-2-hydroxy-propoxy)-5-fluorophenyl]-crotonic acid nitrile hydrochloride melting at 201° to 203° C. are obtained.

EXAMPLE 56

[D,L]-3-[2-(3-N-2*-pyridino-piperazino-2-hydroxy-propoxy)-5-fluorophenyl]-crotonic acid nitrile dihydrochloride 3.7 Grams of 1-(2-pyridyl)-piperazine are added to a solution of 5.0 g of [D,L]-3-[2-(2,3-oxidopropoxy)-5-fluorophenyl]-crotonic acid nitrile in 20 ml of ethanol and the whole is boiled under reflux for 2 hours. The mixture is cooled and concentrated hydrochloric acid is cautiously added to adjust a pH of 4.0. Next, the mixture is evaporated to dryness in vacuo and the crude hydrochloride obtained is purified as described in Example 54. After final recrystallization from isopropanol-/ethanol 4.8 grams of [D,L]-3-[2-(3-N-2*-pyridino-piperazino-2-hydroxy-propoxy)-5-fluoro-phenyl]-crotonic acid nitrile dihydrochloride melting at 131° to 132° C. are obtained.

EXAMPLE 57

[D,L]-3-[3-fluoro-4-(3-[1-methyl-3-phenyl-propyl]-amino)-2-hydroxy-propoxy-phenyl]-crotonic acid nitrile dihydrochloride 1.6 Grams of 1-methyl-3-phenyl-propylamine are added to a solution of 2.17 grams of [D,L]-3-[3-fluoro-4-(2,3-oxidopropoxy)-phenyl]-crotonic acid nitrile in 20 ml of isopropanol, the whole is boiled under reflux for 5 hours and then evaporated to dryness in vacuo. The crude base is digested with ether and filtered off with suction. After drying over phosphorus pentoxide, 3.1 grams of [D,L]-3-[3-fluoro-4-(3-[1-methyl-3-phenyl-propyl]-amino)-2-hydroxy-propoxy-phenyl]-crotonic acid nitrile melting at 98° C. are obtained.

The base is dissolved in just a sufficient amount of dry chloroform and a pH of 4.0 is adjusted by cautiously adding chloroform solution saturated with hydrogen chloride. The mixture is then concentrated in vacuo to a small volume and the precipitated hydrochloride is rapidly filtered off with the exclusion of moisture.

After drying in vacuo, 2.7 grams of hygroscopic [D,L]-3-[3-fluoro-4-(3-[1-methyl-3-phenyl-propyl]-amino)-2-hydroxy-propoxy-phenyl]-crotonic acid nitrile hydrochloride are obtained.

EXAMPLE 58

[D,L]-3-[3-fluoro-4-(3-N-2*-methoxyphenyl-piperazino-2-hydroxy-propoxy)-phenyl]-crotonic acid nitrile dihydrochloride 7.5 Grams of [D,L]-3-[3-fluoro-4-(2,3-oxido-propoxy)-phenyl]-crotonic acid nitrile in 75 ml of isopropanol and 6.23 grams of N-2-methoxy-phenylpiperazine are boiled under reflux for 5 hours.

The mixture is then evaporated to dryness in vacuo and the residue is dissolved in a small amount of dry chloroform and a pH of 3.0 is adjusted with about 9 ml of ether saturated with hydrogen chloride. The mixture is again evaporated to dryness in vacuo. The crude hydrochloride obtained is then purified as described in Example 54. 9.58 Grams of free base melting at 99° to 102° C. are obtained which are transformed into 7.2 grams of [D,L]-3-[3-fluoro-4-(3-N-2*-methoxyphenyl-piperazino-2-hydroxy-propoxy)-phenyl]-crotonic acid nitrile dihydrochloride.

EXAMPLE 59

[D,L]-3-[3-fluoro-4-(3-N-2*-pyridino-piperazino-2-hydroxy propoxy)-5-fluoro-phenyl]-crotonic acid nitrile trihydrochloride 7.5 Grams of [D,L]-3-[3-fluoro-4-(2,3-oxido-propoxy)-phenyl]-crotonic acid nitrile in 75 ml of isopropanol are reacted with 5.29 grams of 1-(2-pyridyl)-piperazine and worked up as described in Example 58. 9.0 Grams of free base melting at 119° C. are obtained which are transformed into 9.2 grams of [D,L]-3-[3-fluoro-4-(3-N-2*-pyridino-piperazino-2-hydroxy-propoxy)-5-fluoro-phenyl]-crotonic acid nitrile trihydrochloride.

EXAMPLE 60

[D,L]-3-[4-(1-methyl-3-phenyl-propyl)-amino-2-hydroxy-propoxy)-phenyl]-crotonic acid nitrile hydrochloride In the manner as described in Example 58, 2.15 grams of [D,L]-3-[4-(2,3-oxido-propoxy)-phenyl]-crotonic acid nitrile in 20 ml of isopropanol are reacted with 1.5 grams of 1-methyl-3-phenyl-propylamine and worked up. 1.4 Grams of free base are obtained melting at 105° C. which are transformed into 1.4 grams [D,L]-3-[4-(1-methyl-3-phenylpropyl)-amino-2-hydroxy-propoxy)-phenyl]-crotonic acid nitrile hydrochloride.

EXAMPLE 61

[D,L]-3-[3-methoxy-4-(3,3*, 4*-dimethoxy-phenethyl-amino-2-hydroxy-propoxy)-phenyl]-crotonic acid nitrile hydrochloride 9.8 Grams of [D,L]-3-[3-methoxy-4-(2,3-oxide-propoxy)-phenyl]-crotonic acid nitrile are heated for 2 hours on a steam bath under reflux.

The mixture is then diluted with about 50 ml of ethanol, adjusted to a pH-value of 1 wtih concentrated hydrochloric acid, and the reaction mixture is poured into 5 liters of water. The neutral constituents are extracted with toluene/ethyl acetate. The aqueous phase is rendered weakly basic with sodium hydrogen carbonate, extracted with toluene and the basic extracts are dried by rotation, and recrystallised from toluene/ether and then from ethanol. Yield: 7.6 grams of free base melting at 115°–116° C. It is converted in the usual manner (see Example 1) into the hydrochloride, and the latter is recrystallised from ethanol/ether and ethanol. Yield: 6.4 grams of [D,L]-3-[3-methoxy-4-(3-3*,4*-dimethoxy-phenethyl-amino-2-hydroxy-propoxy)-phenyl]-crotonic acid nitrile hydrochloride melting at 110°–112° C.

EXAMPLE 62

[D,L]-3-[4-(3-N-2*-methoxyphenyl-piperazino-2-hydroxy-propoxy)-phenyl]-crontonic acid ethyl ester hydrochloride A solution of 15.0 grams of [D,L]-3-[4-(2,3-oxido-propoxy)-phenyl]-crontonic acid ethyl ester and 10.0 grams of N-2-methoxy-phenylpiperazine in 50 ml of ethanol are boiled under reflux for 1 hour. After cooling, a pH of 4 is adjusted by cautiously adding concentrated hydrochloric acid. 20 ml of toluene are added and the whole is evaporated to dryness. After rubbing with a small amount of acetone, the crystals formed are filtered off. The filter residue is suspended in a small amount of ethyl acetate, stirred with a very small amount of water, filtered again and washed with a small amount of ethyl acetate and a small amount of water. The filter residue is dissolved in hot ethanol, digested with a small amount of charcoal, concentrated in vacuo to a small volume and cooled to 0° C. The precipitated crystals are collected and dried at 40° C. in vacuo. 6.2 Grams of [D,L]-3-[4-(3-N-2*-methoxyphenyl-piperazino-2-hydroxy-propoxy)-phenyl]-crotonic acid ethyl ester hydrochloride melting at 183° to 184° C. are obtained.

EXAMPLE 63

[D,L]-3-[4-(3-[3-methoxyphenylethylamino]-2-hydroxy-propoxy)-phenyl]-crotonic acid nitrile hydrochloride 2.15 Grams of [D,L]-3-[4-(2,3-oxido-propoxy)-phenyl]-crotonic acid nitrile and 1.6 grams of 3-methoxyphenylethylamine in 20 ml of isopropanol are boiled under reflux for 5 hours. The mixture is then evaporated to dryness in vacuo and the residue is dissolved in chloroform. After acidification with hydrogen chloride/ether solution, the mixture is again evaporated to dryness and the residue is digested in 2 liters of hot water. The hot solution is filtered to remove insoluble matter and the cooled filtrate is washed with ethyl acetate and then rendered alkaline with soda solution. The mixture is extracted with methylene chloride and, after drying, the extract is concentrated to a small volume. After some standing in the cold, the separated crystals are collected and dried in vacuo. 2.04 g of free base melting at 70° to 72° C. are obtained which, after recrystallization from methylene chloride/hydrogen chloride/ether, are transformed into 1.96 grams of [D,L]-3-[4-(3-[3-methoxyphenylethylamino]-2-hydroxy-propoxy)-phenyl]-crotonic acid nitrile hydrochloride melting at 144° to 145° C.

EXAMPLE 64

[D,L]-3-[4-(3-[4-benzoylamino-piperidino]-2-hydroxy-propoxy)-phenyl]-crotonic acid nitrile hydrochloride 2.15 Grams of [D,L]-3-[4-(2,3-oxido-propoxy)-phenyl]-crotonic acid nitrile and 2.04 grams of 4-benzoylamino-piperidine in 25 ml of isopropanol are boiled under reflux for 5 hours. The mixture is then evaporated to dryness in vacuo, the crystalline residue is rubbed with a small amount of ether and filtered off. 3.8 Grams of free base melting at 160° to 161° C. are obtained, which are transformed as described in Example 63 into 3.4 grams of [D,L]-3-[4-(3-[4-benzoylamino-piperidino]-2-hydroxy-propoxy)-phenyl]-crotonic acid nitrile hydrochloride melting at 224° to 225° C.

EXAMPLE 65

[D,L]-3-[2-(3-3*,4*-Dimethoxy-phenethyl-amino-2-hydroxy-propoxy)-4-fluoro-phenyl]-crotonic acid nitrile hydrochloride 14.0 Grams of [D,L]-3-[2-(2,3-oxido-propoxy)-4-fluoro-phenyl]-crotonic acid nitrile in 15 ml of ethanol are heated with 20.0 grams of homoveratrylamine for 2 hours on a steam bath under reflux, working up is carried out as described in Example 1, and the hydrochloride is recrystallised from isopropanol/ether. Yield: 11.4 grams of [D,L]-3-[2-(3-3*,4*-dimethoxy-phenethyl-amino-2-hydroxy-propoxy)-4-fluorophenyl)-crotonic acid nitrile hydrochloride melting at 153°-155° C.

EXAMPLE 66

[D,L]-3-[2-(3-3*,4*-Dimethoxy-phenethyl-amino-2-hydroxy-propoxy)-5-fluorophenyl]-crotonic acid nitrile hydrochloride 12.0 Grams of [D,L]-3-[2-(2,3-oxido-propoxy)-5-fluorophenyl]-crotonic acid nitrile in 15 ml of ethanol are reacted with 12.0 grams of homoveratrylamine in the manner described in Example 16 e. The 10.6 grams of free base melting at 105°-107° C. first obtained are converted in the usual manner (analogous to Example 1) into 8.8 grams of [D,L]-3-[2-(3-3*,4*-dimethoxy-phenethyl-amino-2-hydroxy-propoxy)-5-fluoro-phenyl]-crotonic acid nitrile hydrochloride melting at 145°-147° C.

EXAMPLE 67

[D,L]-3-[2-(3-3*,4*-Dimethoxy-phenethyl-amino-2-hydroxy-propoxy)-4-methoxy-phenyl]-crotonic acid nitrile hydrochloride 7.0 Grams of [D,L]-3-[2-(2,3-oxido-propoxy)-4-methoxy-phenyl]-crotonic acid nitrile in a mixture of 7.0 grams of homoveratrylamine and 7.0 ml of ethanol are heated on a steam bath (while refluxing) for one hour. The reaction mixture is cautiously adjusted with concentrated hydrochloric acid to a pH-value of 3.5, stirred into 1 l of water and extracted three times with toluene/ethyl acetate. The aqueous phase is then adjusted to a pH-value of 8 to 8.5 with sodium hydrogen carbonate and is again extracted with toluene. The basic extracts are dried, rotated and the crude base is converted into the hydrochloride in the manner described in Example 1.

There were obtained 9.4 grams of [D,L]-3-[2-(3,3*,4*-dimethoxy-phenethylamino-2-hydroxy-propoxy)-4-methoxy-phenyl]-crotonic acid nitrile hydrochloride melting at 169°-170° C.

EXAMPLE 68

[D,L]-3-[2-Methoxy-4-(3,3*,4*-dimethoxy-phenethyl-amino-2-hydroxy-propoxy)-phenyl]-crotonic acid nitrile hydrochloride 6.7 Grams of [D,L]-3-[2-Methoxy-4-(2,3-oxido-propoxy)-phenyl]-crotonic acid nitrile in 7 ml of ethanol are boiled under reflux for one hour with 7.0 grams of homoveratrylamine and reacted as described in Example 14. Yield: 6.6 grams of [D,L]-3-[2-methoxy-4-(3-3*,4*-dimethoxyphenethyl-amino-2-hydroxy-propoxy)-phenyl]-crotonic acid nitrile hydrochloride melting at 131°-132° C.

EXAMPLE 69

[D,L]-3-[3-Chloro-4-(3-3*,4*-dimethoxy-phenethyl-amino-2-hydroxy-propoxy)-phenyl]-crotonic acid nitrile hydrochloride 5.0 Grams of [D,L]-3-[3-Chloro-4-(2,3-oxido-propoxy)-phenyl]-crotonic acid nitrile are boiled under reflux with 15 ml of ethanol and 5 grams of homoveratrylamine for 4 hours. 50 Grams of ethanol are then added, the mixture is adjusted to a pH-value of 3.5 with concentrated hydrochloric acid is poured into 5 liters of water. After extraction of the neutral fraction with ethyl acetate/toluene (2:1), the aqueous phase is rendered weakly alkaline with sodium bicarbonate. Extraction is carried out with toluene/ethyl acetate (2:1) and the organic phase is dried and rotated. By crystallisation with toluene/diisopropyl ether 5.1 grams of free base melting at 117°-119° C., are obtained. The latter is converted into the hydrochloride as described in Example 1. Yield: 4.7 grams of [D,L]-3-[3-chloro-4-(3-3*,4*-dimethoxy-phenethyl-amino-2-hydroxy-propoxy)-phenyl]-crotonic acid nitrile hydrochloride melting at 146°-148° C.

EXAMPLE 70

[D,L]-3-[4-(3-[1-methyl-3-phenylpropyl]-amino)-2-hydroxylpropoxy]-phenyl-crotonic acid nitrile hydrochloride 6.0 Grams of [D,L]-3-[4-(2,3-oxidopropoxy)-phenyl]-crotonic acid nitrile are stirred for 7 hours at 45° to 50° C. in a solution of 4.2 grams of 1-methyl-3-phenyl-propyl-amine in 35 ml of isopropanol in the presence of a small amount of 2 N-sodium hydroxide solution. The mixture is then cooled and, while stirring, a pH of 3.5 is adjusted by cautiously adding concentrated hydrochloric acid dropwise. Crystallisation sets in, which is completed by adding a small amount of ether. The crystals are filtered off with suction, washed with a little ether and dried.

6.3 Grams (56% of the theory) of the hydrochloride are obtained melting at 148° to 152° C.

What is claimed is:

1. A compound of the formula

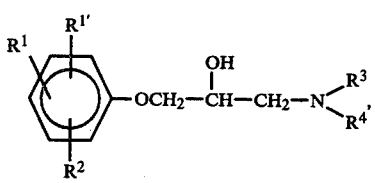

or a physiologically tolerable acid addition salt thereof, wherein $R^1$ and $R^{1'}$ are the same or different and are hydrogen, allyl, halogen, nitro, or alkyl or alkoxy having 1 to 4 carbon atoms; $R^2$ has the formula

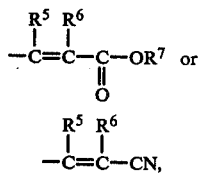

wherein $R^5$ is hydrogen, alkyl having 1 to 5 carbon atoms, aryl, aryl-lower alkyl, or aryl or aryl-lower alkyl substituted by lower alkyl or alkoxy, $R^6$ is hydrogen or alkyl having 1 to 8 carbon atoms, and $R^7$ is hydrogen, lower alkyl, or aryl-lower alkyl; $R^3$, taken alone, is hydrogen; $R^4$, taken alone, is

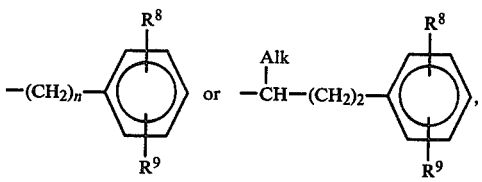

wherein Alk is alkyl having 1 to 3 carbon atoms, n is a number from 1 to 3, $R^8$ and $R^9$, taken alone, are the same or different and are hydrogen, alkoxy having 1 to 3 carbon atoms, or benzyloxy, or $R^8$ and $R^9$, taken together, are bis-methylene-dioxy; or $R^3$ and $R^4$, taken together with the nitrogen atom to which they are attached, are a heterocyclic ring having 5 to 7 members, or such a ring substituted by alkyl having 1 to 4 carbon atoms, or such a ring, unsubstituted or substituted by alkyl having 1 to 4 carbon atoms, wherein one carbon atom may be replaced by oxygen, sulfur, or nitrogen, which latter may be unsubstituted or substituted by alkyl, alkoxy, oxalkyl, acyl, or carbalkoxy each having 1 to 5 carbon atoms, by pyridyl, by phenyl, or by phenyl mono-substituted or poly-substituted by hydroxy, halogen, or alkyl or alkoxy having 1 to 4 carbon atoms.

2. A compound or salt as in claim 1 wherein, if $R^3$, taken alone, is hydrogen, then $R^4$, taken alone, is

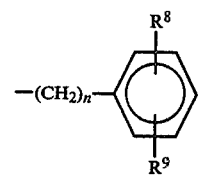

3. A pharmaceutical composition comprising a therapeutically-effective amount of a compound as in claim 1 together with a pharmaceutically suitable carrier therefor.

4. A pharmaceutical composition comprising a therapeutically-effective amount of a compound as in claim 2 together with a pharmaceutically-suitable carrier therefor.

5. A method for treating coronary disease in a patient suffering therefrom which comprises administering to said patient a therapeutically-effective amount of a compound as in claim 1.

6. A method for treating coronary disease in a patient suffering therefrom which comprises administering to said patient a therapeutically-effective amount of a compound as in claim 2.

* * * * *

UNITED STATES PATENT AND TRADEMARK OFFICE
CERTIFICATE OF CORRECTION

PATENT NO. : 4,191,765
DATED : March 4, 1980
INVENTOR(S) : Fritsch et al.

It is certified that error appears in the above-identified patent and that said Letters Patent are hereby corrected as shown below:

Column 3, line 30, in the structural formula, "$NHR_2$" should be --$NHR_4$--;

Column 5, line 56, "Kosolapoff" should be --Kosolapoft--;

Column 5, line 60, "β" should be --α--;

Column 10, line 21, "15" should be --14--;

Column 16, line 18, "3-3A*,4*" should be --3-3*,4*--;

Column 16, line 60, "3-3*,4AA*" should be --3-3*,4*--;

and

Column 17, line 31, "phenylpiperaazino" should be --phenylpiperazino--.

In the Heading, Item 30, "May 25, 1977" should be -- May 25, 1976 -- and "26233147" should be -- 2623314 --.

Signed and Sealed this

Twenty-ninth Day of July 1980

[SEAL]

Attest:

SIDNEY A. DIAMOND

Attesting Officer     Commissioner of Patents and Trademarks